United States Patent [19]
Lassila et al.

[11] Patent Number: 6,103,799
[45] Date of Patent: Aug. 15, 2000

[54] SURFACE TENSION REDUCTION WITH N, N'-DIALKYLALKYLENEDIAMINES

[75] Inventors: Kevin Rodney Lassila, Macungie; Kristen Elaine Minnich; Richard Van Court Carr, both of Allentown, all of Pa.

[73] Assignee: Air Products and Chemicals, Inc., Allentown, Pa.

[21] Appl. No.: 09/009,099

[22] Filed: Jan. 20, 1998

[51] Int. Cl.$^7$ .............................. C08J 3/03; C08L 79/02; C09D 11/00; C09D 5/14

[52] U.S. Cl. .......................... 524/251; 524/252; 523/160; 523/161

[58] Field of Search ................... 523/160, 161; 524/250, 251, 252

[56] References Cited

U.S. PATENT DOCUMENTS

| | | | |
|---|---|---|---|
| 2,267,205 | 12/1941 | Kyrides | 510/276 |
| 2,767,162 | 10/1956 | Cheney | 260/210 |
| 2,868,833 | 1/1959 | Szabo et al. | 260/501 |
| 3,192,113 | 6/1965 | Thomas et al. | 167/65 |
| 3,268,593 | 8/1966 | Carpenter et al. | 260/615 |
| 4,117,249 | 9/1978 | De Simone et al. | 568/252 |
| 4,126,640 | 11/1978 | Floyd | 564/512 |
| 4,322,530 | 3/1982 | Jachimowicz | 544/403 |
| 5,019,166 | 5/1991 | Schwarz | 106/31.43 |
| 5,098,478 | 3/1992 | Krishnan et al. | 106/31.89 |
| 5,562,762 | 10/1996 | Mrvos et al. | 106/106 |
| 5,707,638 | 1/1998 | Lösel et al. | 424/407 |
| 5,804,640 | 9/1998 | Laura et al. | 524/507 |

FOREIGN PATENT DOCUMENTS 0018741 of 0000 European Pat. Off. .

OTHER PUBLICATIONS

March, Jerry; Advanced Organic Chemistry, McGraw Hill, New York (pp. 819–820), 1977.

Y. Murata, et al. "Relationship between the Surface–Active Properties and in vitro Antiplaque Effect of Polyalkylpolymethylenediamines" Caries Research, vol. 24, Apr. 24, 1990, pp. 254–255 S. Karger AG, Basel.

Schwartz, J. "The Importance of Low Dynamic Surface Tension in Waterborne Coatings", Journal of Coatings Technology, Sep. 1992.

Wirth, W., Storp, S., Jacobsen, W. "Mechanisms controlling Leaf Retention of Agicultural Spray Solutions" Pestic. Sci. 1991, 33 411–420.

Medina, S. W.; Sutovich, M. N. "Using Surfactants to Formulate VOC Compliant Waterbased Inks" Am. Ink Maker 1994, 72 (2),. 32–38.

Shepherd, R. G. Wilkenson, R. G., J. Med. Pharm. Chem. 1962, 5, 823–35.

Murata, Y.; Miyamoto, E. Ueda, M. Yakuzaigaku 1989, 49 (4) 327–330.

Murata, Y.; Miyamoto, E.; Kawashima, S. Caries Res. 1990, 24, 254–255.

Primary Examiner—Vasu Jagannathan
Assistant Examiner—Callie E. Shosho
Attorney, Agent, or Firm—Michael Leach

[57] ABSTRACT

This invention provides water-based compositions, particularly coating, ink, and agricultural compositions, manifesting reduced equilibrium and dynamic surface tension by the incorporation of a surface tension reducing amount of certain alkylated diamine compounds of the structure

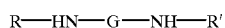

R—HN—G—NH—R' where R and R' are independently C5 to C8 alkyl, and G is a C2–C6 linear or cyclic alkylene group which may contain C1–C4 alkyl substituents.

22 Claims, No Drawings

SURFACE TENSION REDUCTION WITH N,N'-DIALKYLALKYLENEDIAMINES

FIELD OF THE INVENTION

The invention relates to the use of alkylated alkylenediamines to reduce the surface tension in water-based systems.

BACKGROUND OF THE INVENTION

The ability to reduce the surface tension of water is of great importance in waterborne coatings, inks, adhesives, and agricultural formulations because decreased surface tension translates to enhanced substrate wetting in actual formulations. Surface tension reduction in water-based systems is generally achieved through the addition of surfactants. Performance attributes resulting from the addition of surfactants include enhanced surface coverage, fewer defects, and more uniform distribution. Equilibrium surface tension performance is important when the system is at rest. However, the ability to reduce surface tension under dynamic conditions is of great importance in applications where high surface creation rates are utilized. Such applications include spraying of coatings or agricultural formulations, or high speed gravure or ink-jet printing. Dynamic surface tension is a fundamental quantity which provides a measure of the ability of a surfactant to reduce surface tension and provide wetting under such high speed application conditions.

Traditional nonionic surfactants such as alkylphenol or alcohol ethoxylates, and ethylene oxide (EO)/propylene oxide (PO) copolymers have excellent equilibrium surface tension performance but are generally characterized as having poor dynamic surface tension reduction. In contrast, certain anionic surfactants such as sodium dialkyl sulfosuccinates can provide good dynamic results, but these are very foamy and impart water sensitivity to the finished coating.

The objective of this invention is to provide a family of surfactants which provide good equilibrium and dynamic surface tension properties and are low-foaming and thus would be widely accepted in the coating, ink, adhesive, and agricultural formulation industries.

The importance of reducing equilibrium and dynamic surface tension in applications such as coatings, inks, and agricultural formulations is well-appreciated in the art.

Low dynamic surface tension is of great importance in the application of waterborne coatings. In an article, [Schwartz, J. "The Importance of Low Dynamic Surface Tension in Waterborne Coatings", Journal of Coatings Technology, September 1992] there is a discussion of surface tension properties in waterborne coatings and a discussion of dynamic surface tension in such coatings. Equilibrium and dynamic surface tension were evaluated for several surface active agents. It is pointed out that low dynamic surface tension is an important factor in achieving superior film formation in waterborne coatings. Dynamic coating application methods require surfactants with low dynamic surface tensions in order to prevent defects such as retraction, craters, and foam.

Efficient application of agricultural products is also highly dependent on the dynamic surface tension properties of the formulation. In an article, [Wirth, W.; Storp, S.; Jacobsen, W. "Mechanisms Controlling Leaf Retention of Agricultural Spray Solutions"; Pestic. Sci. 1991, 33, 411–420], the relationship between the dynamic surface tension of agricultural formulations and the ability of these formulations to be retained on a leaf was studied. These workers observed a good correlation between retention values and dynamic surface tension, with more effective retention of formulations exhibiting low dynamic surface tension.

Low dynamic surface tension is also important in high-speed printing as discussed in the article "Using Surfactants to Formulate VOC Compliant Waterbased Inks" [Medina, S. W.; Sutovich, M. N. Am. Ink Maker 1994, 72 (2), 32–38]. In this article, it is stated that equilibrium surface tensions (EST's) are pertinent only to ink systems at rest. EST values, however, are not good indicators of performance in the dynamic, high speed printing environment under which the ink is used. Dynamic surface tension is a more appropriate property. This dynamic measurement is an indicator of the ability of the surfactant to migrate to a newly created ink/substrate interface to provide wetting during high speed printing.

U.S. Pat. No. 5,098,478 discloses water-based ink compositions comprising water, a pigment, a nonionic surfactant and a solubilizing agent for the nonionic surfactant. Dynamic surface tension in ink compositions for publication gravure printing must be reduced to a level of about 25 to 40 dynes/cm to assure that printability problems will not be encountered.

U.S. Pat. No. 5,562,762 discloses an aqueous jet ink of water, dissolved dyes and a tertiary amine having two polyethoxylate substituents and that low dynamic surface tension is important in ink jet printing.

U.S. Pat. No. 3,192,113 and Shepherd, R. G.; Wilkenson, R. G. J. Med. Pharm. Chem. 1962, 5, 823–35. disclose a series of N,N'-dialkylethylenediamines and their acid addition salts as active in vivo against *Mycobacterium tuberculosis*. Similar materials are also disclosed in Brit 898,928. No surface active properties of N,N'-dialkylethylenediamines are noted in any of these disclosures.

U.S. Pat. No. 2,868,833 discloses N,N'-dialkylethylenediamines and their salts can be used to isolate and purify penicillin from aqueous solutions.

U.S. Pat. No. 2,767,168 discloses the use of N,N'-dialkylethylenediamines in the purification of streptomycin.

Murata, Y.; Miyamoto, E.; Ueda, M. *Yakuzaigaku* 1989, 49 (4), 327–330 and Murata, Y.; Miyamoto, E.; Kawashima, S. *Caries Res.* 1990, 24, 254–255 disclose surface active properties of dihydrochlorides of N,N'-dialkylpolymethylendiamines of the from

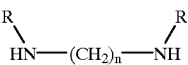

where R is a linear alkyl group of 6 to 10 carbons and n=2 to 5. In these papers, surface tension measurements of dihydrochlorides of N,N'-dialkylpolymethylendiamines were measured using a face surface tensiometer. This measurement provides equilibrium surface tension values which don't provide any indication regarding the efficacy of these materials in applications requiring dynamic performance. The measured equilibrium surface tensions of solutions of the dihydrochlorides of N,N'-dialkylpolymethylenediamines were found to roughly correlate to the killing time for *streptococcus sobrinus* (OMZ 176) and *streptococcus mutans* (MT5091) and to the antiplaque activity of the materials.

U.S. Pat. No. 5,371,288 discloses the MIBK reductive alkylate of 1,3 propanediamine as an intermediate for the preparation of curatives for polyurethane cast elastomers.

SUMMARY OF THE INVENTION

This invention provides water-based compositions containing an organic compound, particularly organic coating, ink, and agricultural compositions, having reduced equilibrium and dynamic surface tension by incorporation of an effective amount of an alkylated diamine compound of the following structure:

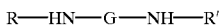

where R and R' are independently C5 to C8 alkyl, and G is a C2–C6 linear or cyclic alkylene group which may contain C1–C4 alkyl substituents.

Also provided is a method for applying a water-based organic compound containing composition to a surface, especially to partially or fully coat the surface with the water-based composition, the composition containing an effective amount of an N,N'-dialkyl alkylenediamine compound of the above structure for reducing the dynamic surface tension of the water-based composition.

There are significant advantages associated with the use of these alkylated diamines in water-based organic coatings, inks, and agricultural compositions and these advantages include:

- an ability to formulate water-borne coatings, inks, and agricultural compositions which may be applied to a variety of substrates with excellent wetting of substrate surfaces including contaminated and low energy surfaces;
- an ability to provide a reduction in coating or printing defects such as orange peel and flow/leveling deficiencies;
- an ability to produce water-borne coatings and inks which have low volatile organic content, thus making these surfactants environmentally favorable;
- an ability to formulate coating and ink compositions capable of high speed application;
- an ability to formulate compositions which retain dynamic surface tension properties under strongly basic, high temperature environments.
- an ability to formulate coatings, inks, and adhesives in which the surfactant is reactive during cure, reducing water sensitivity in the final products which arises from the presence of free surfactant.

Because of their excellent surfactant properties and low foam characteristics, these materials are likely to find use in many applications in which reduction in dynamic and equilibrium surface tension and low foam are important. Such applications include various wet-processing textile operations, such as dyeing of fibers, fiber souring, and kier boiling, where low-foaming properties would be particularly advantageous; they may also have applicability in soaps, water-based perfumes, shampoos, and various detergents where their marked ability to lower surface tension while simultaneously producing substantially no foam would be highly desirable.

DETAILED DESCRIPTION OF THE INVENTION

This invention relates to the use of compounds of the formula

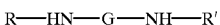

where R and R' are independently C5 to C8 alkyl, and G is a C2–C6 linear or cyclic alkylene group which may contain C1–C4 alkyl substituents, for the reduction of equilibrium and dynamic surface tension in water-based compositions containing an organic compound, particularly coating, ink, and agricultural compositions containing organic compounds such as polymeric resins, herbicides, pesticides or plant growth modifying agents. It is desirable that an aqueous solution of the alkylated polyamine demonstrates a dynamic surface tension of less than 45 dynes/cm at a concentration of ≦5 wt % in water at 23° C. and 1 bubble/second according to the maximum-bubble-pressure method. The maximum-bubble-pressure method of measuring surface tension is described in *Langmuir* 1986, 2, 428–432, which is incorporated by reference.

Suitable alkylene groups include ethylene, propylene, butylene, pentylene, cyclopentylene, hexylene and cyclohexylene optionally containing C1–C4 alkyl substituents such as methyl and ethyl groups. The preferred N,N'-dialkyl alkylenediamines are those in which G is ethylene or propylene.

The alkylated diamines can be prepared by reductive alkylation of diamines with aldehydes and ketones using well-established procedures. The essential aspects of the preparation are the reaction of an aldehyde or ketone with the diamine to make an imine or enamine intermediate which then reacts with hydrogen in the presence of a suitable hydrogenation catalyst to form the corresponding saturated derivative.

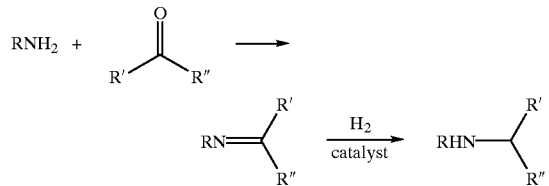

The imine or enamine derivative may be preformed or may be prepared in situ. The reductive alkylation procedure is the method of choice for the production of these materials, but the products may also be prepared by reaction of a diamine derivative with an alkyl halide, or by reaction of a diamine with an alcohol in the presence of a suitable catalyst, all being syntheses well known to an organic chemist.

Diamine starting materials which are suitable for the preparation of the compounds of this invention include 1,2-ethylenediamine, 1,3-propanediamine, 1,2-propanediamine, 1,4-butanediamine, 1,5-pentanediamine, 2-methyl-1,5-pentanediamine, 1,6-hexanediamine and 1,2-cyclohexanediamine.

N,N'-dialkyl alkylenediamines containing three-carbon linking groups may also be prepared by cyanoethylation of suitable amines followed by reductive amination of the nitrile:

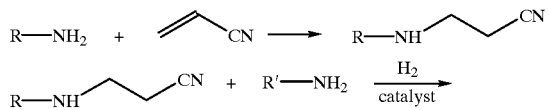

-continued

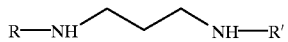

Alternatively, the cyanoethylation product may be reduced to the amine, and a reductive alkylation reaction with a suitable aldehyde or ketone may be performed.

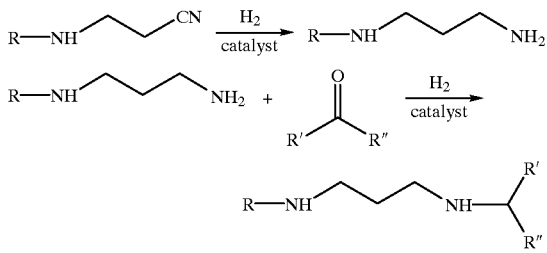

Alkyl groups which are suitable for use on the diamines should have sufficient carbon atoms to confer surface activity (i.e. an ability to reduce the surface tension of water) to the material but not enough carbon atoms to decrease the solubility to the extent that the ability of the material to reduce surface tension is insufficient for a particular application. In general, an increase in the carbon number increases the efficiency of the resulting alkylated diamine surfactant (i.e., less surfactant is required to obtain a given decrease in surface tension) but decreases its ability to reduce surface tension at high surface creation rates (i.e., less effective for reducing dynamic surface tension). The latter effect is a result of the fact that increased carbon number generally decreases the water solubility of the material, and consequently, diminishes the diffusive flux of surfactant to newly-created surface. Generally, in the practice of this invention, it is desirable to use alkylated diamines having a solubility in water of at least 0.005 wt %, preferably from 0.01 to 2 wt %, and most preferably from 0.05 to 1.5 wt %.

The alkyl groups may be the same or different. They may be linear or branched, and the point of attachment to the nitrogen of the diamine may be on either an internal or terminal carbon. Suitable alkyl groups are derived from reductive alkylation reactions of a C5 to C8 aldehyde or ketone, preferably derived from reductive alkylation reactions of methyl isobutyl ketone or methyl isoamyl ketone. Specific examples of suitable C5 to C8 aldehydes and ketones include 1-pentanal, 2-pentanone, 3-pentanone, methyl isopropyl ketone, 1-hexanal, 2-hexanone, 3-hexanone, methyl tert-butyl ketone, ethyl isopropyl ketone, 1-heptanal, 2-methylhexanal, 2-heptanone, 3-heptanone, 4-heptanone, 1-octanal, 2-octanone, 3-octanone, 4-octanone, 2-ethylhexanal, and so on. The specific carbonyl compound and diamine chosen will depend on the surfactant properties required for a particular application.

The alkylated diamines are suitable for use in an aqueous composition comprising in water an inorganic compound which is a mineral ore or a pigment or an organic compound which is a pigment, a polymerizable monomer, such as addition, condensation and vinyl monomers, an oligomeric resin, a polymeric resin, a detergent, a herbicide, a pesticide, or a plant growth modifying agent. An amount of the alkylated diamine compound that is effective to reduce the equilibrium and/or dynamic surface tension of the water-based inorganic and/or organic compound-containing composition is added. Such effective amount may range from 0.001 to 20 g/100 ml, preferably 0.01 to 2 g/100 ml, of the aqueous composition. Naturally, the most effective amount will depend on the particular application and the solubility of the alkylated diamine.

In the following water-based organic coating, ink, and agricultural compositions containing an alkylated diamine according to the invention, the other listed components of such compositions are those materials well known to the workers in the relevant art.

A typical water-based organic coating composition to which the alkylated diamine surfactants of the invention may be added would comprise the following components in an aqueous medium at 30 to 80% solids:

| Typical Water-Based Organic Coating Composition | |
|---|---|
| 0 to 50 wt % | Pigment Dispersant/Grind Resin |
| 0 to 80 wt % | Coloring Pigments/Extender Pigments/Anti-Corrosive Pigments/Other Pigment Types |
| 5 to 99.9 wt % | Water-Borne/Water-Dispersible/Water-Soluble Resins |
| 0 to 30 wt % | Slip Additives/Antimicrobials/Processing Aids/Defoamers |
| 0 to 50 wt % | Coalescing or Other Solvents |
| 0.01 to 10 wt % | Surfactant/Wetting Agent/Flow and Leveling Agents |
| 0.01 to 5 wt % | Alkylated Diamine |

A typical water-based ink composition to which the alkylated diamine surfactants of the invention may be added would comprise the following components in an aqueous medium at 20 to 60% solids:

| Typical Water-Based Ink Composition | |
|---|---|
| 1 to 50 wt % | Pigment |
| 0 to 50 wt % | Pigment Dispersant/Grind Resin |
| 0 to 50 wt % | Clay base in appropriate resin solution vehicle |
| 5 to 99.9 wt % | Water-Borne/Water-Dispersible/Water-Soluble Resins |
| 0 to 30 wt % | Coalescing Solvents |
| 0.01 to 10 wt % | Surfactant/Wetting Agent |
| 0.01 to 10 wt % | Processing Aids/Defoamers/Solubilizing Agents |
| 0.01 to 5 wt % | Alkylated Diamine |

A typical water-based agricultural composition to which the alkylated diamine surfactants of the invention may be added would comprise the following components in an aqueous medium at 0.1 to 80% ingredients:

| Typical Water-Based Agricultural Composition | |
|---|---|
| 0.1 to 50 wt % | Pesticide or Plant Growth Modifying Agent |
| 0.01 to 10 wt % | Surfactant |
| 0 to 5 wt % | Dyes |
| 0 to 20 wt % | Thickeners/Stabilizers/Co-surfactants/Gel Inhibitors/Defoamers |
| 0 to 25 wt % | Antifreeze |
| 0.1 to 50 wt % | Alkylated Diamine |

EXAMPLE 1

This example illustrates the preparation of the reductive alkylation product of 1,2-ethylenediamine and methyl isobutyl ketone (EDA/MIBK).

1,2-Ethylenediamine (1.6 mole), methyl isobutyl ketone (3.7 mole) and 5% Pd/C (2 wt % of total charge) were charged to a one liter stainless steel autoclave. The reactor was sealed and purged with nitrogen then hydrogen. The contents of the reactor were heated to 90° C. under 7 bar (100 psig) $H_2$. The pressure was increased to 55 bar (800 psig) and maintained throughout the reaction (31 hours) by the admission of hydrogen from a 1 gallon ballast on demand by a dome regulator. The reactor contents were analyzed by GC/FID and found to be 87.6 area % N,N'-dialkylated ethylenediamine. The product was purified by distillation at 112–114° C., 6.6 millibar (5 Torr).

EXAMPLE 2

This example illustrates the preparation of the reductive alkylation product of 1,3-propanediamine and methyl isobutyl ketone (PDA/MIBK).

1,3-Propanediamine (1.0 mole), methyl isobutyl ketone (2.2 mole) and 10% Pd/C (4 wt % of total charge) were charged to a one liter stainless steel autoclave and reacted as in Example 1 for 5 hours. The reactor contents were analyzed by GC/FID and found to be 92.6 area % N,N'-dialkylated 1,3-propanediamine. The product was purified by distillation at 113–115° C., 2.7 millibar (2 Torr).

EXAMPLE 3

This example illustrates the preparation of the reductive alkylation product of a butane-, cyclohexane- and hexanediamine mixture.

A 1,6-hexanediamine process byproduct stream containing a mixture of 1,4-butanediamine, 1,2-cyclohexanediamine, and 1,6-hexanediamine (0.9 mole), methyl isobutyl ketone (2.0 mole) and 10% Pd/C (4 wt % of total charge) were charged to a one liter stainless steel autoclave and reacted as in Example 1 for 4 hours. The reactor contents were analyzed by GC/FID and found to be 11.3 area % monoalkylated 1,2-cyclohexanediamine and 77.4% dialkylated materials. The monoalkylated product was removed by distillation at 126–128° C., 2.7 millibar (2 Torr). The dialkylated product was purified by distillation at 130–137° C., 1.3 millibar (1 Torr) to provide a sample containing (GC FID area % analysis) the reductive alkylation products of 1,4-butanediamine (11.5%), 1,2-cyclohexandiamine (46.6%), and 1,6-hexanediamine (38.7%). The structures of these materials are shown below.

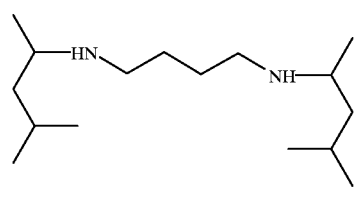

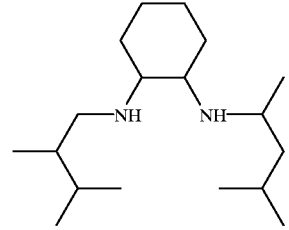

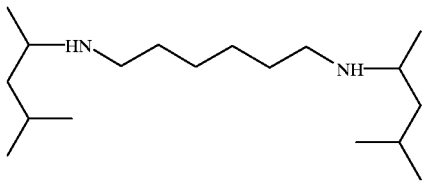

In the following examples dynamic surface tension data were generated for aqueous solutions of the indicated compounds using the maximum-bubble-pressure method at the indicated bubble rates, i.e., bubbles/second (b/s), and room temperature of about 23° C. The equipment used was a Kruss BP 2 bubble pressure tensiometer.

COMPARATIVE EXAMPLE 4

An aqueous solution of the dihydrochloride of EDA/MIBK (Example 1) was prepared by adding 0.1026 g of the diamine, 102.6 g of water, and 0.0878 g of 37% HCl to a suitable container. The molar ratio of diamine to HCl used in this example is 1:2; that is, sufficient acid was added to produce the dihydrochloride of the EDA/MIBK reductive alkylation product. Dynamic surface tension data were obtained for a 0.1 wt % aqueous solution of the dihydrochloride using the maximum bubble pressure method at bubble rates from 0.1 to 20 b/s. These data provide information about the performance of a surfactant at conditions from near-equilibrium (0.1 b/s) through extremely high surface creation rates (20 b/s). In practical terms, high bubble rates correspond to high printing speeds in lithographic or ink-jet printing, high spray or roller velocities in coating applications, and rapid application rates for agricultural products. The data are set forth in Table 1.

TABLE 1

| | EDA-MIBK Dihydrochloride | | | | |
| --- | --- | --- | --- | --- | --- |
| | Dynamic Surface Tension (dyne/cm) | | | | |
| Concentration | 0.1 b/s | 1 b/s | 6 b/s | 15 b/s | 20 b/s |
| 0.1 wt % | 70.3 | 70.7 | 71.0 | 71.1 | 70.1 |

The surface tensions of this solution are nearly indistinguishable from those of water. The poor ability of this material to reduce the surface tension of water was surprising based upon the work of Murata which states that similar dihydrochlorides may function as cationic surfactants.

EXAMPLE 5

A solution in distilled water of the reductive alkylation product of 1,2-ethylene-diamine and methyl isobutyl ketone (EDA/MIBK; Ex 1) was prepared and its dynamic surface tension properties were measured using the procedure described above. The data are set forth in Table 2.

TABLE 2

EDA/MIBK.

| Concentration | Dynamic Surface Tension (dyne/cm) | | | | |
|---|---|---|---|---|---|
| (wt %) | 0.1 b/s | 1 b/s | 6 b/s | 15 b/s | 20 b/s |
| 0.1 | 32.0 | 32.5 | 33.7 | 35.7 | 35.9 |

These results show that at a concentration of 0.1 wt %, the surface tension at 0.1 b/s was 32.0 dyne/cm and, at the high surface creation rate of 20 b/s, the surface tension of the solution of the compound of Example 1 was 35.9 dyne/cm. That this material had surface activity would not be anticipated based on the teachings of the prior art. Furthermore, it is surprising that the performance of this material was so good under dynamic conditions.

EXAMPLE 6

A solution in distilled water of the reductive alkylation product of 1,3-propane-diamine and methyl isobutyl ketone (PDA/MIBK; Ex 2) was prepared and its dynamic surface tension properties were measured using the procedure described above. The data are set forth in Table 3.

TABLE 3

PDA/MIBK.

| | Dynamic Surface Tension (dyne/cm) | | | | |
|---|---|---|---|---|---|
| Concentration | 0.1 b/s | 1 b/s | 6 b/s | 15 b/s | 20 b/s |
| 0.1 wt % | 31.3 | 31.8 | 33.1 | 34.8 | 35.5 |

These results show that at a concentration of 0.1 wt %, the surface tension at 0.1 b/s was 31.3 dyne/cm and, at the high surface creation rate of 20 b/s, the surface tension of the solution of the compound of Example 2 was 35.5 dyne/cm. The performance of this material was good under dynamic conditions.

EXAMPLE 7

Solutions in distilled water of the reductive dialkylation product prepared in Example 3 were prepared and their dynamic surface tension properties were measured using the procedure described above. The data are set forth in Table 4.

TABLE 4

Ex 3 Dialkyated Diamine.

| Concentration | Dynamic Surface Tension (dyne/cm) | | | | |
|---|---|---|---|---|---|
| (wt %) | 0.1 b/s | 1 b/s | 6 b/s | 15 b/s | 20 b/s |
| 0.1 | 40.3 | 42.1 | 45.3 | 48.2 | 48.4 |
| 0.5 | 34.5 | 35.0 | 36.2 | 37.1 | 37.5 |
| 1.0 | 32.3 | 32.6 | 33.7 | 33.9 | 33.4 |

These results illustrate that a reduction in surface tension can be obtained through the use of a mixed material containing linking groups of C4, C6, and cyclohexyl. Although the efficiency of this material is not good as those derived from ethylene-diamine and 1,3-propanediamine, and relatively high use levels are required to obtain an equivalent reduction in surface tension, this product is derived from an extremely inexpensive byproduct stream.

EXAMPLE 8

The foaming properties of a 0.1 wt % solution of the reductive alkylation product of ethylenediamine with methyl isobutyl ketone (Example 1) was examined using a procedure based upon ASTM D 1173-53. In this test, a 0.1 wt % solution of the surfactant is added from an elevated foam pipette to a foam receiver containing the same solution. The foam height is measured at the completion of the addition ("Initial Foam Height") and the time required for the foam to dissipate is recorded ("Time to 0 Foam"). This test provides a comparison between the foaming characteristics of various surfactant solutions. In general, in coatings, inks, and agricultural formulations, foam is undesirable because is complicates handling and can lead to coating and print defects, and to inefficient application of agricultural materials.

TABLE 5

| Compound | Initial Foam Height (cm) | Time to 0 Foam |
|---|---|---|
| EDA/MIBK; Ex 1 | 1.0 | 1 sec |
| PDA/MIBK; Ex 2 | 0.8 | 2 sec |
| Mixture/MIBK; Ex 3 | 1.7 | 3 sec |

The data in Table 5 show that the compounds of this invention form foam which dissipates quickly. Thus it would be expected that these materials would have the requisite properties for use in coatings, inks and agricultural formulations.

The ability of a surfactant in aqueous systems to reduce surface tension under both equilibrium and dynamic conditions is of great importance in the performance of water-based coatings, inks, adhesives, and agricultural formulations. Low equilibrium surface tension allows the development of excellent properties subsequent to application. Low dynamic surface tension results in enhanced wetting and spreading under the dynamic conditions of application, resulting in more efficient use of the formulations and fewer defects. In waterborne coatings, inks, adhesives, and agricultural formulations, the formation of foam is generally undesirable because it complicates handling and can cause defects or result in inefficient application.

STATEMENT OF INDUSTRIAL APPLICATION

The invention provides material suitable for reducing the equilibrium and dynamic surface tension in water-based compositions.

We claim:

1. In a method for applying a water-based composition to a surface, the composition containing an inorganic compound which is a mineral ore or a pigment or an organic compound which is a pigment, a polymerizable monomer, an oligomeric resin, a polymeric resin, a detergent, a herbicide, a pesticide, or a plant growth modifying agent and an effective amount of a surfactant for reducing the dynamic surface tension and the foaming of the composition, the improvement which comprises employing as the surfactant an alkylated diamine of the structure

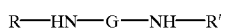

R—HN—G—NH—R' where R and R' are independently C5 to C8 alkyl, and G is a C2–C6 linear or cyclic alkylene group which may contain C1–C4 alkyl substituents.

2. The method of claim 1 in which an aqueous solution of the alkylated diamine demonstrates a dynamic surface tension of less than 45 dynes/cm at a concentration of ≦5 wt % in water at 23° C. and 1 bubble/second according to the maximum-bubble-pressure method.

3. The method of claim 2 in which the alkylene group is ethylene or propylene.

4. The method of claim 2 in which the alkylene group is ethylene.

5. The method of claim 2 in which the measurement is made at 20 bubbles/second.

6. The method of claim 1 in which the alkylated diamine is the reductive alkylation product of ethylenediamine and methyl isobutyl ketone.

7. The method of claim 1 in which the alkylated diamine is the reductive alkylation product of ethylenediamine and methyl isoamyl ketone.

8. The method of claim 1 in which the alkylated diamine is the reductive alkylation product of 1,3-propylenediamine and methyl isobutyl ketone.

9. The method of claim 1 in which the alkylated diamine is the reductive alkylation product of 1,4-butanediamine, 1,2-cyclohexanediamine, 1,6-hexanediamine or any mixture thereof.

10. The method of claim 1 in which the alkylated diamine is present at 0.01 to 2 g/100 ml of the water-based composition.

11. An aqueous composition comprising in water an inorganic compound which is a mineral ore or a pigment or an organic compound which is a pigment, a polymerizable monomer, an oligomeric resin, a polymeric resin, a detergent, a herbicide, a pesticide, or a plant growth modifying agent and an effective amount of an alkylated diamine for reducing the dynamic surface tension of the composition, the alkylated diamine having a structure according to the formula:

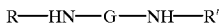

where R and are independently C5 to C8 alkyl, and G is a C2–C6 linear or cyclic alkylene group which may contain C1–C4 alkyl substituents.

12. The composition of claim 11 in which an aqueous solution of the alkylated diamine demonstrates a dynamic surface tension of less than 45 dynes/cm at a concentration of ≦5 wt % in water at 23° C. and 1 bubble/second according to the maximum-bubble-pressure method.

13. The composition of claim 12 in which the alkylene group is ethylene or propylene.

14. The composition of claim 12 in which the alkylene group is ethylene.

15. The composition of claim 11 in which the alkylated diamine is the reductive alkylation product of ethylenediamine and methyl isobutyl ketone.

16. The composition of claim 11 in which the alkylated diamine is the reductive alkylation product of ethylenediamine and methyl isoamyl ketone.

17. The composition of claim 11 in which the alkylated diamine is the reductive alkylation product of 1,3-propylenediamine and methyl isobutyl ketone.

18. The composition of claim 11 in which the alkylated diamine is the reductive alkylation product of 1,4-butanediamine, 1,2-cyclohexanediamine, 1,6-hexanediamine or any mixture thereof.

19. The composition of claim 11 which is an organic coating composition of 30 to 80 wt % components, which components comprise 0 to 50 wt % pigment dispersant, grind resin or mixtures thereof;

0 to 80 wt % coloring pigment, extender pigment, anti-corrosive pigment, other pigment types or mixtures thereof;

5 to 99.9 wt % water-borne, water-dispersible or water-soluble resin or mixtures thereof;

0 to 30 wt % slip additive, antimicrobial agent, processing aid, defoamer or mixtures thereof;

0 to 50 wt % coalescing or other solvents;

0.01 to 10 wt % surfactant, wetting agent, flow and leveling agents or mixtures thereof; and 0.01 to 5 wt % alkylated diamine.

20. The composition of claim 11 which is an ink composition of 20 to 60 wt % components, which components comprise 1 to 50 wt % pigment;

0 to 50 wt % pigment dispersant, grind resin or mixtures thereof;

0 to 50 wt % clay base in a resin solution vehicle;

5 to 99 wt % water-borne, water-dispersible or water-soluble resin or mixtures thereof;

0 to 30 wt % coalescing solvent;

0.01 to 10 wt % processing aid, defoamer, solubilizing agent or mixtures thereof;

0.01 to 10 wt % surfactant, wetting agent or mixtures thereof; and 0.01 to 5 wt % alkylated diamine.

21. The composition of claim 10 which is an agricultural composition of 0.1 to 80 wt % components, which components comprise 1 to 50 wt % pesticide, plant growth modifying agent or mixtures thereof;

0 to 5 wt % dye;

0 to 20 wt % thickener, stabilizer, co-surfactant, gel inhibitor, defoaming agent or mixtures thereof;

0 to 25 wt % antifreeze;

0 to 50 wt % coalescing or other solvents;

0.01 to 10 wt % surfactant; and 0.1 to 50 wt % alkylated diamine.

22. The aqueous composition of claim 11 in which the alkylated diamine is present at 0.01 to 2 g/100 ml of the aqueous composition.

* * * * *

UNITED STATES PATENT AND TRADEMARK OFFICE
CERTIFICATE OF CORRECTION

PATENT NO. : 6,103,799
DATED : January 20, 1998
INVENTOR(S) : Kevin R. Lassila

It is certified that error appears in the above-identified patent and that said Letters Patent is hereby corrected as shown below:

<u>Column 11,</u>
Line 39 should read: "where R and R' are independently C5 to C8 alkyl, and G is a".

Signed and Sealed this

Twenty-fifth Day of December, 2001

*Attest:*

*Attesting Officer*

JAMES E. ROGAN
*Director of the United States Patent and Trademark Office*